(12) United States Patent
Nifant'ev et al.

(10) Patent No.: US 7,579,417 B2
(45) Date of Patent: Aug. 25, 2009

(54) METALLOCENE COMPOUNDS

(75) Inventors: Ilya Nifant'ev, Moscow (RU); Pavel V. Ivchenko, Moscow (RU); Ilya V. Tajdakov, Moscow (RU); Luigi Resconi, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 138 days.

(21) Appl. No.: 10/584,003

(22) PCT Filed: Nov. 16, 2004

(86) PCT No.: PCT/EP2004/012984

§ 371 (c)(1),
(2), (4) Date: Jun. 22, 2006

(87) PCT Pub. No.: WO2005/063828

PCT Pub. Date: Jul. 14, 2005

(65) Prior Publication Data

US 2007/0112152 A1  May 17, 2007

Related U.S. Application Data

(60) Provisional application No. 60/532,331, filed on Dec. 22, 2003.

(30) Foreign Application Priority Data

Dec. 22, 2003 (EP) .................................. 03104913

(51) Int. Cl.
C08F 4/64 (2006.01)
C08F 4/72 (2006.01)
B01J 31/38 (2006.01)

(52) U.S. Cl. .................. 526/172; 526/161; 526/943; 526/941; 526/348.6; 526/351; 526/352; 502/103; 502/104; 556/53; 549/41; 549/59

(58) Field of Classification Search .................. 556/53; 502/103, 104; 526/160, 170, 943, 941, 172, 526/161

See application file for complete search history.

(56) References Cited

U.S. PATENT DOCUMENTS

| 5,830,821 | A | * | 11/1998 | Rohrmann et al. .......... 502/117 |
| 6,004,897 | A | * | 12/1999 | Imuta et al. ................. 502/103 |
| 6,228,795 | B1 | | 5/2001 | Vizzini |
| 7,112,638 | B2 | * | 9/2006 | Nifant'ev et al. ............. 526/160 |
| 2003/0008984 | A1 | | 1/2003 | Kratzer et al. |
| 2003/0013913 | A1 | | 1/2003 | Schottek et al. |

FOREIGN PATENT DOCUMENTS

| DE | 199 62 814 | 6/2001 |
| DE | 199 62 910 | 7/2001 |
| EP | 754 698 A2 * | 1/1997 |
| EP | 754698 | 1/1997 |
| WO | 91/02012 | 2/1991 |
| WO | 92/00333 | 1/1992 |
| WO | 99/21899 | 5/1999 |
| WO | 01/21674 | 3/2001 |
| WO | WO 01/47939 A1 * | 7/2001 |
| WO | 01/62764 | 8/2001 |

OTHER PUBLICATIONS

S. Jüngling et al., "The Role of Dormant Sites in Propene Polymerization Using Methylalumoxane Activated Metallocene Catalysts," *Macromol. Symp.*, vol. 97, p. 205-216 (1995) XP000542005.

Ng. Ph. Buu-Hoï et al., "180. Side-chain Bromination of Some Alkylnaphthalenes with N-Bromosuccinimide," *J. Chem Soc.*, p. 830-832 (1946).

M. Gorsane et al., "Helicenes: Synthese Photochimique de Fluoro-1-Pentahelicenes," *Bull. Soc. Chim. Belg.*, vol. 94(3), p. 205-214 (1985).

G. Porzi et al., "Halogen-Metal Interconversion in 2,7-Dibromonaphthalene and 2,7-Dibromoanthracene," *J. Organometallic Chemistry*, vol. 128, p. 95-98 (1977).

* cited by examiner

*Primary Examiner*—Ling-Siu Choi
*Assistant Examiner*—Rip A. Lee
(74) *Attorney, Agent, or Firm*—Jarrod N. Raphael

(57) ABSTRACT

A metallocene compound of formula (I) wherein: M is an atom of a transition metal; X, same or different, is a hydrogen atom, a halogen atom, or a R, OR, $OSO_2CF_3$, OCOR, SR, $NR_2$ or $PR_2$ group, wherein R is $C_1$-$C_{40}$ hydrocarbon group; L is a divalent bridging group; $R^1$, is a $C_1$-$C_{40}$ hydrocarbon group; $R^3$ is a $C_1$-$C_{40}$ hydrocarbon group; $R^2$, $R^4$, $R^5$, $R^6$, $R^7$ and $R^8$, equal to or different from each other, are hydrogen atoms or $C_1$-$C_{40}$ hydrocarbon groups.

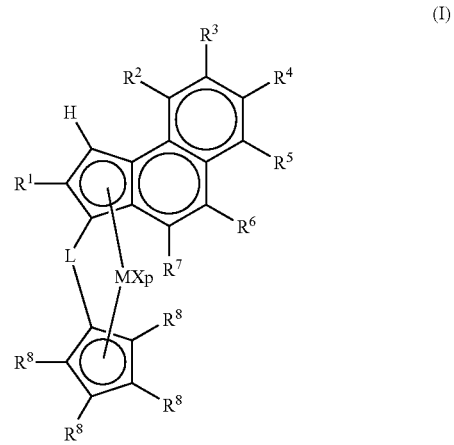

(I)

14 Claims, No Drawings

METALLOCENE COMPOUNDS

The present invention relates to metallocene compounds containing a benzoindenyl moiety having a well-defined substitution pattern. The invention further relates to the use of said metallocene compounds as catalyst components for the polymerization of olefins and the polymerization process thereof.

For the purpose of the present invention the numeration of the positions of the benzoindenyl and indenyl moieties is as set forth below in the moieties of formula (a) and (b):

(a)

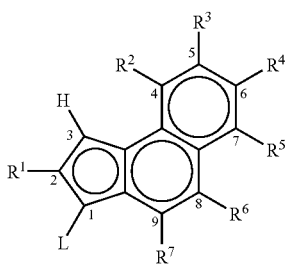

(b)

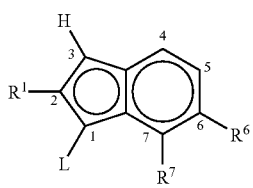

Metallocene compounds containing a benzoindenyl moiety are known from U.S. Pat. No. 5,830,821. However, even if in this document the general formula embraces a plethora of substituted benzoindenyl-containing metallocene compounds, the compounds exemplified are not substituted in position 5 of the benzoindenyl ring.

EP 754 698 discloses dimethylsilylene(2,7-dimethyl-4,5-(2-methyl-benzo)-1-indenyl)(2,7-di-t-butyl-9-fluorenyl)zirconium dicloride. As reported in table 1 this compound has a polymerization activity lower than the correspondent unsubstituted benzoindeny compound.

U.S. Pat. No. 6,228,795 reports, in a long list of compounds, phenyl(methyl)silandiylbis(2-methyl-4,5-(methylbenzo)-1-indenyl)Zr(CH$_3$)$_2$, and phenyl(methyl)silandiylbis(2-methyl-4,5-(tetramethylbenzo)-1-indenyl)Zr(CH$_3$)$_2$. In the first compound no indications are given about the position of the methyl group, that on the contrary as shown in the comparative examples of the present invention is important for improving the activity of these metallocene compounds when used in polymerization reactions.

The applicant found that it is possible to increase the polymerization activity of a metallocene compound containing a 4,5-benzoindenyl moiety, when it is used as catalyst component for the polymerization of olefins, by substituting the 4,5-benzoindenyl moiety in position 5.

An object of the present invention is a metallocene compound of formula (I):

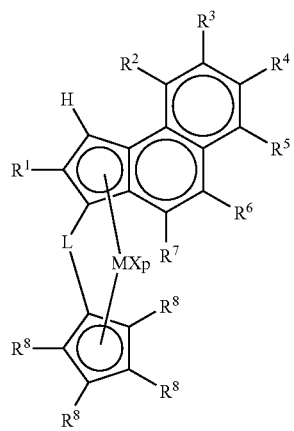

(I)

wherein:

M is an atom of a transition metal selected from those belonging to group 3, 4, 5, 6 or to the lanthanide or actinide groups in the Periodic Table of the Elements; preferably M is titanium, zirconium or hafnium;

p is an integer from 0 to 3, preferably p is 2, being equal to the formal oxidation state of the metal M minus 2;

X, same or different, is a hydrogen atom, a halogen atom, or a R, OR, OSO$_2$CF$_3$, OCOR, SR, NR$_2$ or PR$_2$ group, wherein R is a C$_1$-C$_{40}$ hydrocarbon group optionally containing heteroatoms belonging to groups 13-17 of the Periodic Table of the Elements; preferably R is a linear or branched, cyclic or acyclic, C$_1$-C$_{40}$-alkyl, C$_2$-C$_{40}$ alkenyl, C$_2$-C$_{40}$ alkynyl, C$_6$-C$_{40}$-aryl, C$_7$-C$_{40}$-alkylaryl or C$_7$-C$_{40}$-arylalkyl radicals; optionally containing heteroatoms belonging to groups 13-17 of the Periodic Table of the Elements; or two X can optionally form a substituted or unsubstituted butadienyl radical or a OR'O group wherein R' is a divalent radical selected from C$_1$-C$_{40}$ alkylidene, C$_6$-C$_{40}$ arylidene, C$_7$-C$_{40}$ alkylarylidene and C$_7$-C$_{40}$ arylalkylidene radicals; preferably X is a hydrogen atom, a halogen atom or a R group; more preferably X is chlorine or a methyl radical;

L is a divalent bridging group selected from C$_1$-C$_{20}$ alkylidene, C$_3$-C$_{20}$ cycloalkylidene, C$_6$-C$_{20}$ arylidene, C$_7$-C$_{20}$ alkylarylidene, or C$_7$-C$_{20}$ arylalkylidene radicals optionally containing heteroatoms belonging to groups 13-17 of the Periodic Table of the Elements, and silylidene radical containing up to 5 silicon atoms such as SiMe$_2$, SiPh$_2$; preferably L is a group Z(R")$_2$ wherein Z is a carbon or a silicon atom, and R" is a linear or branched, cyclic or acyclic, C$_1$-C$_{10}$-alkyl, C$_2$-C$_{10}$ alkenyl, C$_2$-C$_{10}$ alkynyl, C$_6$-C$_{10}$-aryl, C$_7$-C$_{10}$-alkylaryl or C$_7$-C$_{10}$-arylalkyl radicals optionally containing heteroatoms belonging to groups 13-17 of the Periodic Table of the Elements; more preferably the group Z(R")$_2$ is Si(CH$_3$)$_2$, SiPh$_2$, SiPhMe, SiMe(SiMe$_3$), CH$_2$, (CH$_2$)$_2$, and C(CH$_3$)$_2$;

R$^1$, is a C$_1$-C$_{40}$ hydrocarbon group optionally containing heteroatoms belonging to groups 13-17 of the Periodic Table of the Elements; preferably R$^1$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; more preferably $R^1$ is linear or branched, saturated or unsaturated $C_1$-$C_{20}$-alkyl radical; even more preferably $R^1$ is a methyl, an ethyl or an isopropyl radical;

$R^3$ is a $C_1$-$C_{40}$ hydrocarbon group optionally containing heteroatoms belonging to groups 13-17 of the Periodic Table of the Elements; preferably $R^3$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; more preferably $R^3$ is linear or branched, saturated or unsaturated $C_1$-$C_{20}$-alkyl or a $C_6$-$C_{40}$-aryl, radical; even more preferably $R^3$ is a methyl, an ethyl or a phenyl radical;

$R^2$, $R^4$ and $R^5$, equal to or different from each other, are hydrogen atoms or $C_1$-$C_{40}$ hydrocarbon groups optionally containing heteroatoms belonging to groups 13-17 of the Periodic Table of the Elements; with the proviso that least one among $R^2$, $R^4$ and $R^5$ is a hydrogen atom; preferably $R^2$, $R^4$ and $R^5$, equal to or different from each other, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals; optionally containing heteroatoms belonging to groups 13-17 of the Periodic Table of the Elements; with the proviso that least one among $R^2$, $R^4$ and $R^5$ is a hydrogen atom; more preferably $R^2$, $R^4$ and $R^5$ are hydrogen atoms;

$R^3$ with $R^4$ and/or $R^4$ with $R^5$ can also join to form a aliphatic or aromatic 3-7 membered ring optionally containing heteroatoms belonging to groups 13-16 of the Periodic Table of the Elements; said ring can bear one or more hydrocarbon substituents having from 1 to 20 carbon atoms;

$R^6$ and $R^7$, equal to or different from each other, are hydrogen atoms or $C_1$-$C_{40}$ hydrocarbon groups optionally containing heteroatoms belonging to groups 13-17 of the Periodic Table of the Elements; preferably $R^6$ and $R^7$, equal to or different from each other, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals; optionally containing heteroatoms belonging to groups 13-17 of the Periodic Table of the Elements; more preferably $R^6$ and $R^7$ are hydrogen atoms or linear or branched, saturated or unsaturated $C_1$-$C_{20}$-alkyl radicals; even more preferably $R^6$ and $R^7$ are hydrogen atoms or a methyl radicals;

$R^8$, equal to or different from each other, are hydrogen atoms or $C_1$-$C_{50}$ hydrocarbon groups optionally containing heteroatoms belonging to groups 13-17 of the Periodic Table of the Elements; two or more $R^8$ groups can also join together to form one or more 3-7 membered rings, said rings contain at least one heteroatom belonging to groups 13-16 of the Periodic Table of the Elements; said rings can be further substituted with $C_1$-$C_{20}$ hydrocarbon groups optionally containing heteroatoms belonging to groups 13-17 of the Periodic Table of the Elements;

A subclass of the compound of formula (I) is a compound of formula (II)

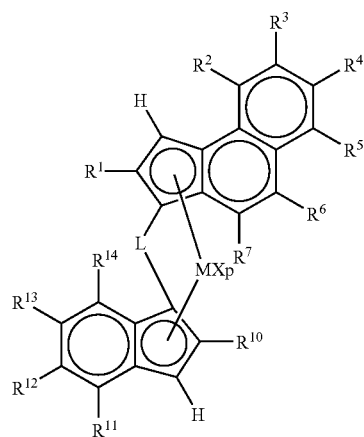

(II)

wherein M, X, p, L $R^1$, $R^2$, $R^3$, $R^4$, $R^5$, $R^6$ and $R^7$ have been described above;

$R^{10}$ is, a hydrogen atom or $C_1$-$C_{40}$ hydrocarbon group optionally containing heteroatoms belonging to groups 13-17 of the Periodic Table of the Elements; preferably $R^{10}$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; more preferably $R^{10}$ is a linear or branched $C_1$-$C_{20}$-alkyl radical such as a methyl radical, an ethyl radical or an isopropyl radical; preferably $R^1$ and $R^{10}$ are not branched $C_1$-$C_{40}$-alkyl radical at the same time.

$R^{11}$, $R^{12}$, $R^{13}$ and $R^{14}$, equal to or different from each other, are hydrogen atoms or $C_1$-$C_{40}$ hydrocarbon groups optionally containing heteroatoms belonging to groups 13-17 of the Periodic Table of the Elements; preferably $R^{11}$, $R^{12}$, $R^{13}$ and $R^{14}$, equal to or different from each other, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals; optionally containing heteroatoms belonging to groups 13-17 of the Periodic Table of the Elements; two adjacent $R^{11}$, $R^{12}$, $R^{13}$ and $R^{14}$ groups can also join to form a 3-7 membered ring optionally containing heteroatoms belonging to groups 13-16 of the Periodic Table of the Elements; said ring can bear one or more hydrocarbon substituents having from 1 to 20 carbon atoms; more preferably $R^{11}$ is a $C_6$-$C_{40}$-aryl, $C_7$-$C_{40}$-alkylaryl or $C_7$-$C_{40}$-arylalkyl radical or form with $R^{12}$ a phenyl ring that can be substituted with hydrocarbon groups having from 1 to 20 carbon atoms;

more preferably $R^{12}$ is a hydrogen atoms or form with $R^{11}$ 3-7 membered ring as explained above;

more preferably $R^{14}$ and $R^{13}$ are hydrogen atoms or $C_1$-$C_{20}$ alkyl radicals.

A preferred class of compounds of formula (II) is a compound of formula (III)

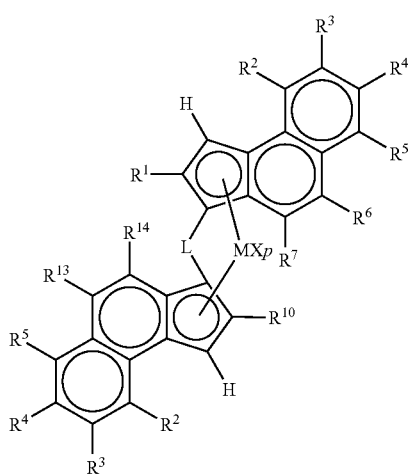

wherein M, X, p, L R$^1$, R$^2$, R$^3$, R$^4$, R$^5$, R$^6$, R$^7$, R$^{10}$, R$^{13}$ and R$^{14}$ have been described above. A further subclass of the compound of formula (I) is a compound of formula (IV)

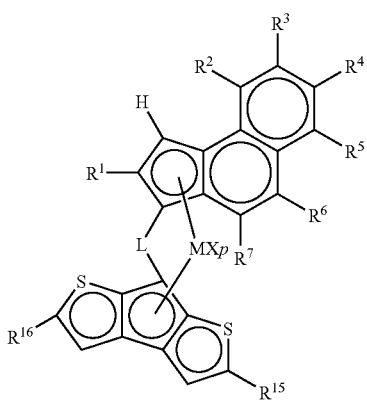

wherein M, X, p, L R$^1$, R$^2$, R$^3$, R$^4$, R$^5$, R$^6$ and R$^7$ have been described above; R$^{15}$ and R$^{16}$, equal to or different from each other, are hydrogen atoms or C$_1$-C$_{40}$ hydrocarbon groups optionally containing heteroatoms belonging to groups 13-17 of the Periodic Table of the Elements; preferably R$^{15}$ and R$^{16}$, equal to or different from each other, are hydrogen atoms or linear or branched, cyclic or acyclic, C$_1$-C$_{40}$-alkyl, C$_2$-C$_{40}$ alkenyl, C$_2$-C$_{40}$ alkynyl, C$_6$-C$_{40}$-aryl, C$_7$-C$_{40}$-alkylaryl or C$_7$-C$_{40}$-arylalkyl radicals; optionally containing heteroatoms belonging to groups 13-17 of the Periodic Table of the Elements; more preferably R$^{15}$ and R$^{16}$ are linear or branched C$_1$-C$_{40}$-alkyl radicals optionally containing heteroatoms belonging to groups 13-17 of the Periodic Table of the Elements such as methyl, ethyl, isopropyl or trimethylsilyl radicals.

The metallocene compounds of formula (I) can be obtained with the process comprising the following steps:
(a) contacting the compound of formula (Ia)

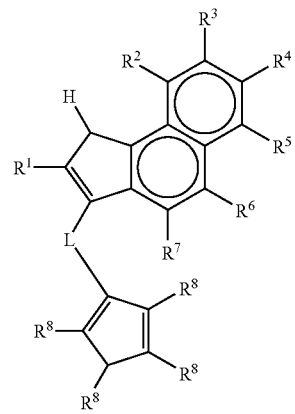

and/or its double bond isomers
wherein R$^1$, R$^2$, R$^3$, R$^4$, R$^5$, R$^6$, R$^7$, R$^8$ and L have the meaning described above with a base selected from T$_j$B, TMgT$^1$, sodium and potassium hydride, metallic sodium and potassium, wherein B is an alkaline or alkali-earth metal; and j is 1 or 2, j being equal to 1 when B is an alkaline metal, preferably lithium, and j being equal to 2 when B is an alkali-earth metal; T is a linear or branched, cyclic or acyclic, C$_1$-C$_{20}$-alkyl, C$_6$-C$_{20}$-aryl, C$_7$-C$_{20}$-alkylaryl or C$_7$-C$_{20}$-arylalkyl radical, optionally containing one or more Si or Ge atoms; preferably T is methyl or butyl radical; T$^1$ is an halogen atom or a group OR''' wherein R''' is a linear or branched, cyclic or acyclic, C$_1$-C$_{40}$-alkyl, C$_6$-C$_{40}$-aryl, C$_7$-C$_{40}$-alkylaryl or C$_7$-C$_{40}$-arylalkyl radical, optionally containing one or more heteroatoms belonging to groups 13-17 of the Periodic Table of the Elements; preferably T$^1$ is an halogen atom, more preferably bromine; wherein the molar ratio between said base and the ligand of the formula (Ia) and is at least 2:1; excess of said base can be used; and
a) contacting the product obtained in step a) with a compound of formula MX$_{p+2}$ wherein M, X and p have the meaning described above.

The ligands of formula (Ia) can be obtained with a process comprising the following steps:
a) contacting a compound of formula (VI):

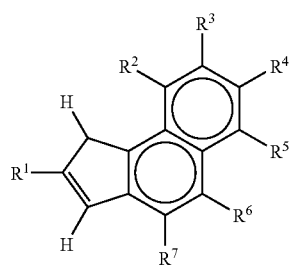

and/or its double bond isomer
wherein R$^1$, R$^2$, R$^3$, R$^4$, R$^5$ R$^6$ and R$^7$ are defined as above; with a base selected from T$_j$B, TMgT$^1$, sodium and potassium hydride, metallic sodium and potassium; wherein T, j, B and $T^1$ are defined as above, and wherein the molar ratio between said base and the compound of the formula (VI) is at least 1:1; excess of said base can be used;

b) contacting the anionic compound obtained in step a) with a compound of formula (VII):

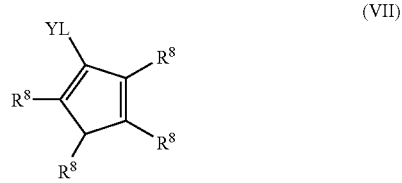

(VII)

wherein $R^8$ and L are defined as above and Y is chlorine, bromine and iodine, preferably Y is chlorine or bromine.

An alternative process for preparing the ligand of formula (I) comprises the following steps:

a) contacting a compound of formula (VIIa):

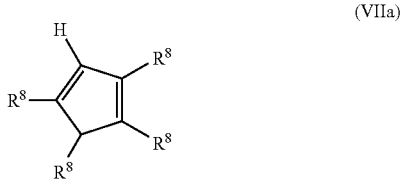

(VIIa)

and/or its double bond isomer
wherein $R^8$ is defined as above;
with a base selected from $T_jB$, $TMgT^1$, sodium and potassium hydride, metallic sodium and potassium; wherein T, j, B and $T^1$ are defined as above, and wherein the molar ratio between said base and the compound of the formula (VIIa) is at least 1:1; excess of said base can be used;

b) contacting the anionic compound obtained in step a) with a compound of formula (VIa):

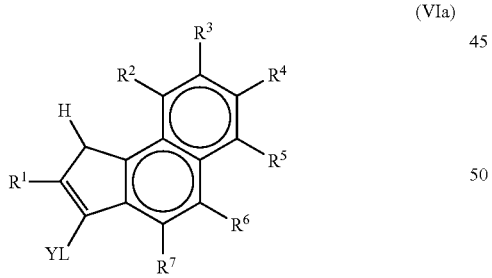

(VIa)

wherein $R^1$, $R^2$, $R^3$, $R^4$, $R^5$, $R^6$, $R^7$ and L are defined as above and Y is chlorine, bromine and iodine, preferably Y is chlorine or bromine.

The above processes are preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

A further object of the present invention is a ligand of formula (Ia)

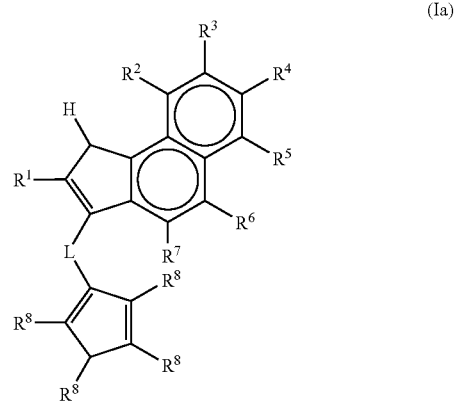

(Ia)

and/or its double bond isomers wherein $R^1$, $R^2$, $R^3$, $R^4$, $R^5$, $R^6$, $R^7$, $R^8$ and L have the meaning described above.

Metallocene compounds of formulas (II) (III) (IV) can be prepared by using the process described above starting respectively from the ligands of formulas (IIa), (IIIa) and (IVa) and/or their double bonds isomers:

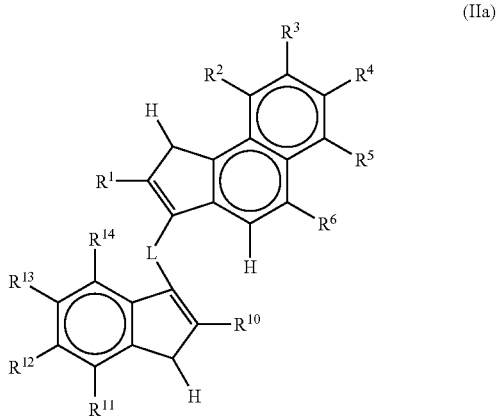

(IIa)

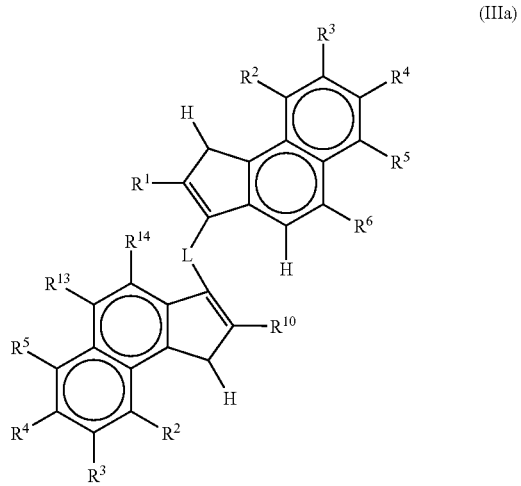

(IIIa)

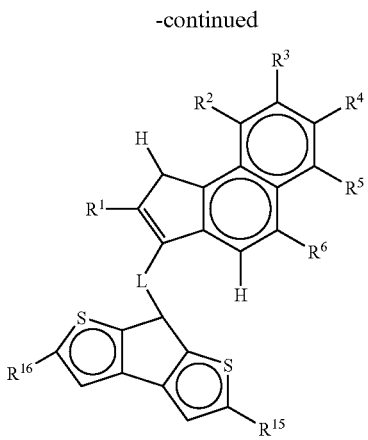
(IVa)

wherein LX $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, have been described above.

The ligand of formulas (IIa), (IIIa), and (IVa) can be prepared according to the process described above by using the corresponding starting compounds.

The compounds of formula (VI) and (VIa) can be prepared according to U.S. Pat. No. 5,830,821, by using the opportunely substituted naphtalene moiety as starting compound.

The metallocene compounds object of the present invention can be used as catalyst components for obtaining a catalyst system for the polymerization of olefins. Therefore a further object of the present invention is a catalyst system obtainable by contacting:

a) at least a metallocene compound of formula (I);

b) at least an alumoxane or a compound able to form an alkylmetallocene cation; and c) optionally an organo aluminum compound.

Preferably at least a metallocene compound of formulas (II), (III) and (IV) is used.

Alumoxanes used as component b) can be obtained by reacting water with an organo-aluminium compound of formula $H_jAlU_{3-j}$ or $H_jAl_2U_{6-j}$, where the U substituents, same or different, are hydrogen atoms, halogen atoms, $C_1$-$C_{20}$-alkyl, $C_3$-$C_{20}$-cyclalkyl, $C_6$-$C_{20}$-aryl, $C_7$-$C_{20}$-alkylaryl or $C_7$-$C_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The molar ratio between aluminium and the metal of the metallocene is generally comprised between about 10:1 and about 30000:1, preferably between about 100:1 and about 5000:1.

The alumoxanes used in the catalyst according to the invention are considered to be linear, branched or cyclic compounds containing at least one group of the type:

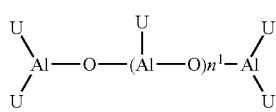

wherein $n^1$ is 0 or an integer of from 1 to 40 and the substituents U are defined as above; and/or a group of the type:

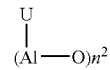

in the case of cyclic compounds, wherein $n^2$ is an integer from 2 to 40 and the U substituents are defined as above.

Examples of alumoxanes suitable for use according to the present invention are methylalumoxane MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl) aluminium (TDMBA) and tris(2,3,3-trimethylbutyl) aluminium (TTMBA) are preferred.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be removed by an olefinic monomer. Preferably, the anion $E^-$ comprises one or more boron atoms. More preferably, the anion E⁻ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylbenzylammonium-tetrakispentafluorophenylborate,
N,N-Dimethylhexylamonium-tetrakispentafluorophenylborate,
N,N-Dimethylaniliniumtetra(phenyl)borate,
N,N-Diethylaniliniumtetra(phenyl)borate,
N,N-Dimethylaniliniumtetrakis(pentafluorophenyl)borate,
N,N-Dimethylaniliniumtetrakis(pentafluorophenyl)aluminate,
N,N-Dimethylbenzylammonium-tetrakispentafluorophenylborate,
N,N-Dimethylhexylamonium-tetrakispentafluorophenylborate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphonium tetrakis(phenyl)borate,
Triphenylcarbeniumtetrakis(pentafluorophenyl)borate,
Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate, and
N,N-Dimethylaniliniumtetrakis(pentafluorophenyl)borate.

Organic aluminum compounds used as compound c) are those of formula $H_jAlU_{3-j}$ or $H_jAl_2U_{6-j}$ as described above.

The catalyst system object of the present invention can be used for (co)polymerizing one or more olefins. Therefore a further object of the present invention is a process for (co)polymerizing olefins containing from 2 to 20 carbon atoms comprising contacting one or more of said olefins under polymerization conditions in the presence of the catalyst system described above. Preferably alpha-olefins containing from 2 to 20 carbon atoms are used.

Examples of alpha-olefins that can be used with the process of the present invention are: ethylene, propylene, 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene and 1-eicosene. Preferred olefins are propylene, ethylene and 1-butene.

The following examples are given for illustrative purpose and do not intend to limit the invention.

EXAMPLES

General Procedures

All operations were performed under nitrogen by using conventional Shlenk-line techniques. Solvents were purified by degassing with nitrogen and passing over activated $Al_2O_3$ and stored under nitrogen. All compounds were analyzed by $^1H$-NMR and $^{13}C$-NMR on a DPX 200 Bruker spectrometer. Due to the low solubility of the Zirconocene, the $^{13}C$-NMR spectra of this compound were performed on a Bruker DPX 400 in $CD_2Cl_4$ at 120° C.

The melting points of the polymers ($T_m$) were measured by Differential Scanning Calorimetry (D.S.C.) on Perkin Elmer DSC-7 instrument, according to the standard method. A weighted sample (5-10 mg) obtained from the polymerization was sealed into aluminum pans and heated at 200° C. with a scanning speed corresponding to 20° C./minute. The sample was kept at 200° C. for 5 minutes to allow a complete melting of all the crystallites. Successively, after cooling to 0° C. with a scanning speed corresponding to 20° C./minute the sample was kept for 5 minutes at 0° C. Then the sample was heated for the second time at 200° C. with a scanning speed corresponding to 10° C./min. In this second heating run, the peak temperature was taken as the melting temperature ($T_m$).

Comparative Example 1

(dimethyl)silanedyilbis(4,5-benzo-indenyl)Zirconiumdichloride (C1)

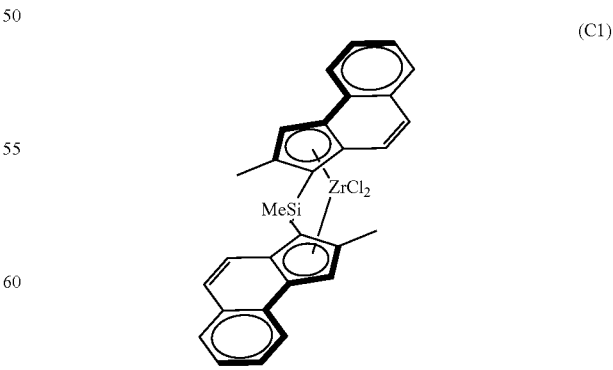

was prepared according to the procedure described in U.S. Pat. No. 5,830,821.

Comparative Example 2

Synthesis of (dimethyl)silanedyilbis(2,7-dimethyl-3H-cyclopenta[a]naphthalen-1-yl)ZrCl₂ (C2)

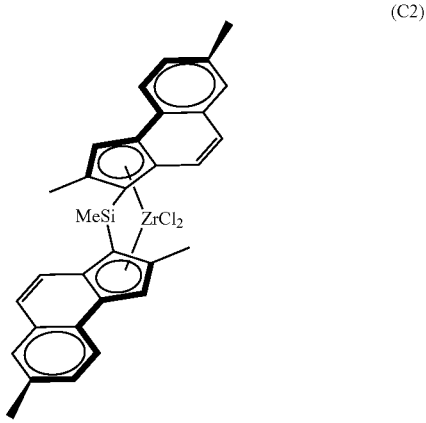

(C2)

a)
2-methyl-2-[(6-methyl-2-naphthyl)methyl]malonic acid

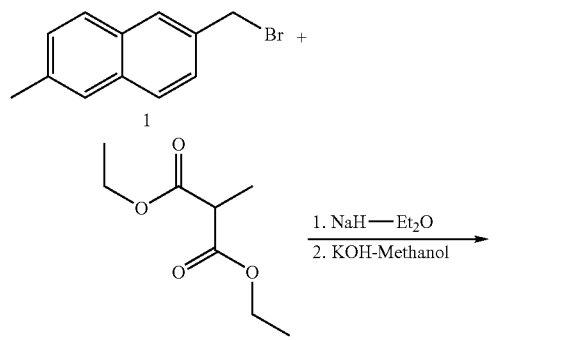

To a stirred suspension of 3.6 g NaH (90 mmol, 60% in mineral oil) in 200 ml Et₂O 16.2 ml (94 mmol) of diethyl 2-methylmalonate was added slowly with cooling. After 2 h stirring at 20 C, solution of 21.2 g (90 mmol) of 2-(bromomethyl)-6-methylnaphthalene (prepared according Buu-Hoi L.; *J. Chem. Soc.;* 1946; 831) in 30 ml of THF was added, resulting mixture was stirred overnight and decomposed by addition of saturated NH₄Cl solution. Organic phase was separated, aqueous—extracted twice with 100 ml portions of ether. Combined extracts were evaporated, residue was dissolved in 150 ml methanol and solution of KOH (20 g, 360 mmol) was added slowly. Mixture was refluxed for 5 h, then evaporated to dryness and resulting semisolid was dissolved in warm water (400 ml). Solution was extracted three times with 100 ml portions of ether, then acidified by carefully addition of 10% HCl. Precipitate of acid 2 was collected and dried, yielded 20 g (81%) of white powder.

H¹NMR (dmso-d₆): 12.9 (broad s, 2H), 7.72 (m, 2H), 7.62 (d, 2H), 7.33 (m, 2H), 3.3 (s, 2H), 2.4 (s, 3H), 1.25 (s, 3H).

b) 2,7-dimethyl-2,3-dihydro-1H-cyclopenta[a]naphthalen-1-one

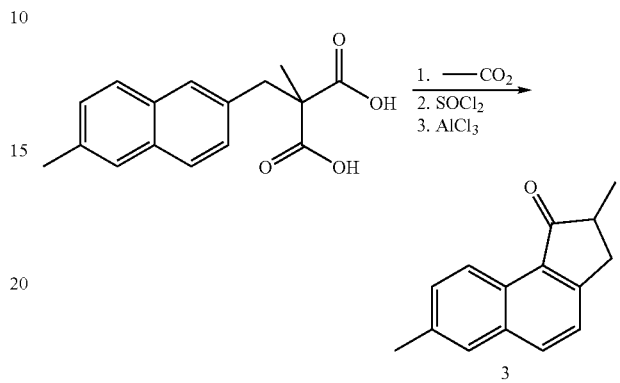

Acid 2 (20 g, 73 mmol) was heated to 180 C without solvent until gas evolving ceased (10 min), then reaction mixture was cooled, dissolved in benzene (50 ml) end evaporated. Oily residue was again dissolved in benzene (100 ml) and treated with SOCl₂ (16 ml, 219 mmol). Resulting solution was refluxed 3 h, evaporated to dryness and dissolved in 100 ml of dry CH₂C₂. This solution was added dropwise at 0 C to stirred suspension of 14.5 g (109 mmol) anhydrous AlCl₃ in 50 ml of CH₂Cl₂. Reaction mixture was stirred overnight, poured into ice-5% HCl solution and extracted twice with 50 ml of CH₂Cl₂. Combined organic extracts were washed with KHCO₃ solution, dried over MgSO₄ and evaporated, afforded 11.4 g (74%) of 3 as brown semisolid.

H¹NMR (CDCl₃): 9.05 (d, 1H), 7.95 (d, 1H), 7.68 (s, 1H), 7.52 (d, 1H), 7.45 (d, 2H), 3.45 (qwart, 1H), 2.8 (m, 2H), 2.55 (s, 3H), 1.40 (d, 3H).

c) 2,7-dimethyl-3H-cyclopenta[a]naphthalene

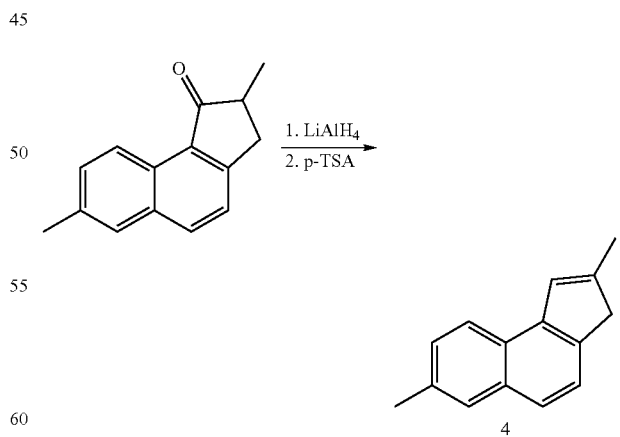

To a suspension of 0.54 g (14 mmol) LiAlH₄ in 50 ml Et₂O solution of 10 g (48 mmol) of 3 in ether was added slowly with stirring at 0 C. Reaction mixture was stirred at room temperature for 4 h, then decompose by addition of saturated NH₄Cl solution. Organic layer was separated, evaporated and resulting oil was dissolved in 250 ml of benzene. Small amount (100 mg) of p-TSA was added and solution was refluxed with Dean-Stark water trap for 1 h. Reaction was monitored by TLC (benzene). Dark solution was cooled, washed with saturated $KHCO_3$ solution, dried over $MgSO_4$, filtered through $Al_2O_3$ (Fluka, neutral, grade I) layer and evaporated. Yield of 4 (two isomers) as light semisolid—8.1 g (87%).

$H^1NMR$ ($CDCl_3$): 8.05 (d, 1H), 7.85 (d, 1H), 7.74 (m, 3H), 7.64 (m, 2H), 7.55 (d, 1H), 7.4 (m, 2H), 7.15 ("s", 1H), 6.7 ("s", 1H), 3.65 (s, 2H), 3.55 (s, 2H), 2.63 (d, 6H), 2.33 (d, 6H).

d) bis(2,7-dimethyl-3H-cyclopenta[a]naphthalen-1-yl)(dimethyl)silane

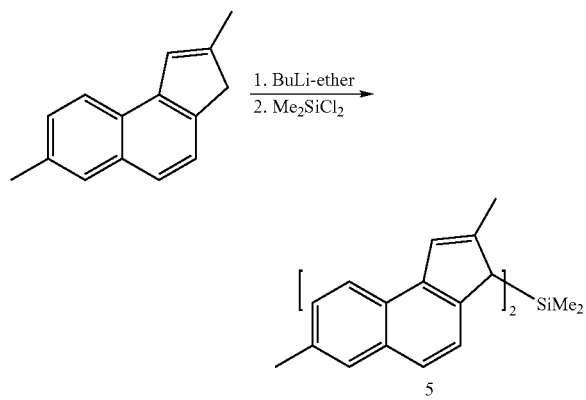

Lithium salt of 4 was prepared in usual manner from 5 g (25.7 mmol) of 4 and 17 ml (27.2 mmol) n-BuLi (Merck, 1.6 N solution in hexanes) in 75 ml $Et_2O$ at −30 C. Then reaction mixture was warmed to 20 C, stirred 5 h and again cooled to −70 C. At this temperature 130 mg (1.4 mmol, 5% mol) of CuCN was added, resulted suspension stirred for 20 min and 1.55 ml (12.8 mmol) of $Me_2SiCl_2$ was added at one portion. Stirring was continued overnight, then mixture was poured into cold water, extracted with benzene (2*100 ml). Benzene solution was filtered through silicagel (Merck 60) and evaporated, yielded 4.7 g (83%) as light solid (mixture of rac- and meso-isomers).

$H^1NMR$ ($CDCl_3$): 8.15, 7.75, 7.6, 7.45 (m, Σ20H), 7.3 (s, 4H), 4.1 (d, 4H), 2.61 (s, 12H), 2.4 (d, 12H), −0.2 (s, 3H, meso-), −0.27 (s, 6H, rac-), −0.29 (s, 3H, meso-)

e) (dimethyl)silanedyilbis(2,7-dimethyl-3H-cyclopenta[a]naphthalen-1-yl)ZrCl₂

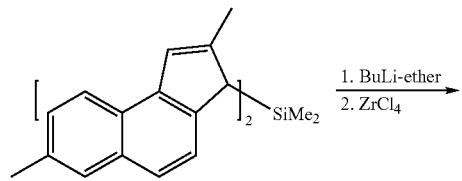

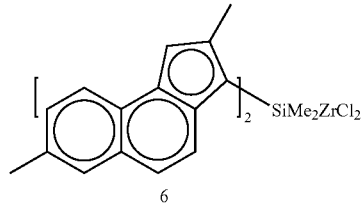

Lithium salt of 5 was prepared from 3 g (6.75 mmol) of 5 and 8.8 ml (14.4 mmol) n-BuLi (Merck, 1.6 N solution in hexanes) in 40 ml of $Et_2O$ at −30 C. Then reaction mixture was warmed to 20 C, stirred 1 h and evaporated. Dry salt was suspended in 100 ml of pentane, then consecutively 1.86 g $ZrCl_4$ (7.9 mmol) and 5 ml of $Et_2O$ was added and mixture was stirred overnight. Precipitate was filtered off, washed with pentane and dried. Resulted compound was recrystallised from dichloromethane-ether mixture, afforded 6 as yellow-orange powder. Yield 2.5 g of 6 as a mixture of rac-/meso-=5/1.

$H^1NMR$ ($CD_2Cl_2$): 7.85, 7.6, 7.4, 7.32, 7.35, (m, Σ20H), 7.2 (s, 2H), 7.07 (s, 2H) 2.53 (s, 12H), 2.40 (s, 6H), 2.34 (s, 6H), 2.35 (s, 6H), 1.43 (s, 3H, meso-), 1.33 (s, 6H, rac-), 1.24 (s, 3H, meso-)

Example 1

Synthesis of (dimethyl)silanedyilbis(2,8-dimethyl-3H-cyclopenta[a]naphthalen-1-yl)ZrCl₂ (A1)

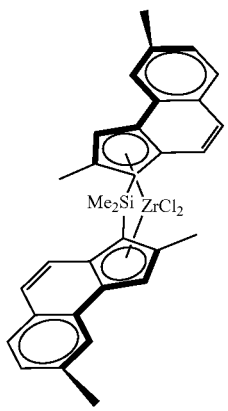

a)
2-methyl-2-[(7-methyl-2-naphthyl)methyl]malonic acid

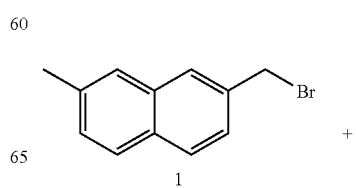

-continued

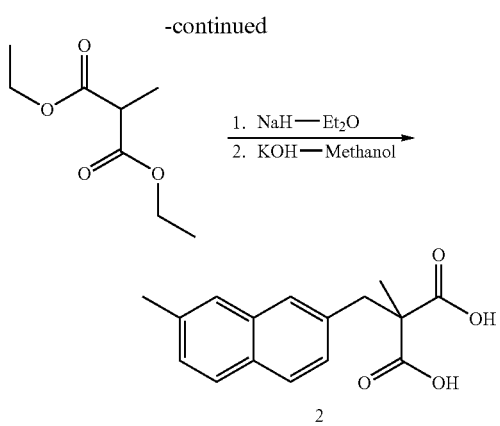

To a stirred suspension of 3.6 g NaH (90 mmol, 60% in mineral oil) in 200 ml Et₂O 16.2 ml (94 mmol) of diethyl 2-methylmalonate was added slowly with cooling. After 2 h stirring at 20 C, solution of 21.2 g (90 mmol) of 2-(bromomethyl)-7-methylnaphthalene (prepared according Gorsane, M.; Martin, R. H.; *Bull. Soc. Chim. Belg.;* 94; 3; 1985; 205-214.) in 20 ml of THF was added, resulting mixture was stirred overnight and decomposed by addition of saturated NH₄Cl solution. Organic phase was separated, aqueous—extracted twice with 100 ml portions of ether. Combined extracts were evaporated, residue was dissolved in 150 ml methanol and solution of KOH (20 g, 360 mmol) was added slowly. Mixture was refluxed for 5 h, then evaporated to dryness and resulting semisolid was dissolved in warm water (300 ml). Solution was extracted three times with 100 ml portions of ether, then acidified carefully by addition of 10% HCl. Precipitate of acid 2 was collected and dried, yielded 18.8 g (76%) of yellowish powder.

H¹NMR (CDCl₃): 7.77 (qwart, 2H), 7.62 (s, 2H), 7.33 (m, 2H), 2.9 (s, 2H), 2.56 (s, 3H), 1.26 (s, 3H)

b) 2,8-dimethyl-2,3-dihydro-1H-cyclopenta[a]naphthalen-1-one

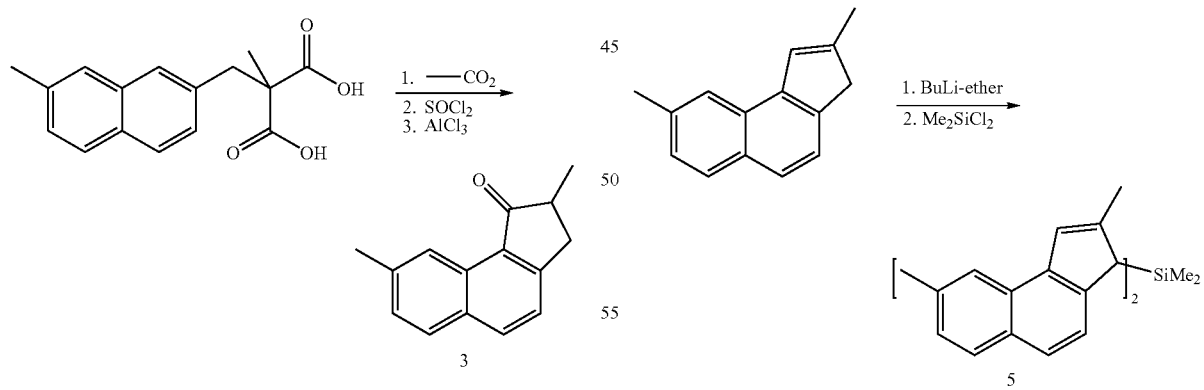

Acid 2 (15 g, 55 mmol) was heated to 180 C without solvent until gas evolving ceased (10 min), then reaction mixture was cooled, dissolved in benzene (50 ml) end evaporated. Oily residue was again dissolved in benzene (100 ml) and treated with SOCl₂ (12 ml, 165 mmol). Resulting solution was refluxed 3 h, evaporated to dryness and dissolved in 100 ml of dry CH₂Cl₂. This solution was added dropwise at 0 C to stirred suspension of 11.1 g (83 mmol) anhydrous AlCl₃ in 50 ml of CH₂Cl₂. Reaction mixture was stirred overnight, poured into ice-5% HCl solution and extracted twice with 50 ml of CH₂Cl₂. Combined organic extracts were washed with KHCO₃ solution, dried over MgSO₄ and evaporated, afforded 9.6 g (83%) of 3 as brown solid.

H¹NMR (CDCl₃): 9.0 (s, 1H), 8.0 (d, 1H), 7.8 (d, 1H), 7.45 (t, 2H), 3.45 (qwar, 1H), 2.8 (m, 2H), 2.6 (s, 3H), 1.4 (d, 3H).

c) 2,8-dimethyl-3H-cyclopenta[a]naphthalene

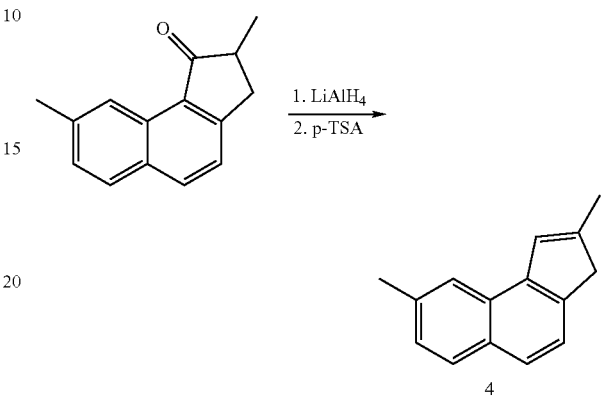

To a suspension of 0.32 g (8 mmol) LiAlH₄ in 10 ml Et₂O solution of 3.5 g (17 mmol) of 3 in ether (50 ml) was added slowly with stirring at 0 C. Reaction mixture was stirred at room temperature for 4 h, then decompose by addition of saturated NH₄Cl solution. Organic layer was separated, evaporated and resulting oil was dissolved in 250 ml of benzene. Small amount (100 mg) of p-TSA was added and solution was refluxed with Dean-Stark water trap for 1 h. Reaction was monitored by TLC (benzene). Dark solution was cooled, washed with saturated KHCO₃ solution, dried over MgSO₄ and evaporated. Yield of 4 (two isomers) as light semisolid—2.5 g (76%).

H¹NMR (CDCl₃): 7.82 (t, 4H), 7.60 (d, 2H), 7.51 (d, 2H), 7.31 (t, 2H), 7.10 (s, 2H), 3.47 (s, 4H), 2.58 (s, 6H), 2.3 (s, 6H)

d) bis(2,8-dimethyl-3H-cyclopenta[a]naphthalen-1-yl)(dimethyl)silane

Lithium salt of 4 was prepared in usual manner from 2.0 g (10.3 mmol) of 4 and 6.8 ml (10.8 mmol) n-BuLi (Merck, 1.6 N solution in hexanes) in 3.0 ml Et₂O at −30 C. Then reaction mixture was warmed to 20 C, stirred 2 h and again cooled to −70 C. At this temperature 60 mg (0.6 mmol, 5% mol) of CuCN was added, resulted suspension stirred for 20 min and 0.62 ml (5.13 mmol) of Me₂SiCl₂ was added at one portion. Stirring was continued overnight, then mixture was poured into cold water, extracted with benzene (2*100 ml). Benzene solution was filtered through silica gel (Merck 60) and evaporated, yielded 1.8 g (79%) as light solid (mixture of rac- and meso-isomers).

H$^1$NMR (CDCl$_3$): 7.9, 7.8, 7.75, 7.55, 7.35 (m, Σ20H), 7.29 (s, 4H), 4.05 (d, 4H), 2.61 (s, 12H), 2.4 (d, 12H), −0.21 (s, 3H, meso-), −0.29 (s, 6H, rac-), −0.30 (s, 3H, meso-)

e) (dimethyl)silanedyilbis(2,8-dimethyl-3H-cyclopenta[a]naphthalen-1-yl)ZrCl$_2$

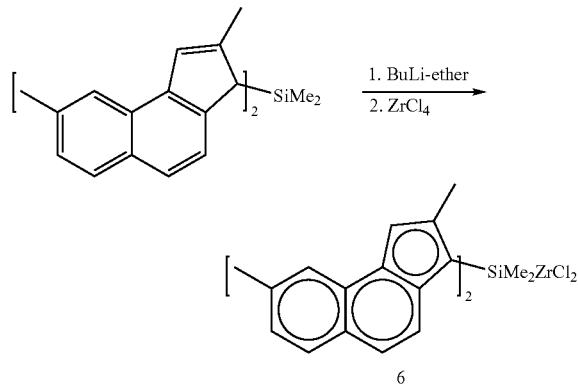

Lithium salt of 5 was prepared from 2.4 g (5.4 mmol) of 5 and 7 ml (11.2 mmol) n-BuLi (Merck, 1.6 N solution in hexanes) in 40 ml of Et$_2$O at −30 C. Then reaction mixture was warmed to 20 C, stirred 1 h and evaporated. Dry salt was suspended in 50 ml of pentane, then consecutively 1.52 g ZrCl$_4$ (6.5 mmol) and 5 ml of Et$_2$O was added and mixture was stirred overnight. Precipitate was filtered off, washed with pentane and dried. Resulted compound was recrystallised from dichloromethane-ether mixture, afforded 6 as yellow powder. Yield of 6 is 1.87 g as a mixture of rac-/meso-=6/4.

H$^1$NMR (CD$_2$Cl$_2$): 7.65, 7.55, 7.35, 7.2, 7.35, 7.1 (m, Σ24H), 2.53 (s, 6H), 2.50 (s, 6H), 2.44 (s, 6H), 2.35 (s, 6H), 1.4 (s, 3H, meso-), 1.35 (s, 6H, rac-), 1.2 (s, 3H, meso)

Example 2

Synthesis of {μ-(η$^5$-2,8-Dimethyl-3H-cyclopenta[a]naphth-3-yl)(η$^5$-2,5-dimethyldithiophenocyclopentadien-7-yl)dimethylsilanediyl] dichlorozirconium (IV) (A2)

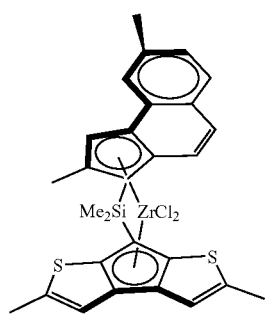

a)(2,8-Dimethyl-3H-cyclopenta[a]naphth-3-yl)(2,5-dimethyl-dithiopheno cyclopentadien-7-yl)dimethylsilane

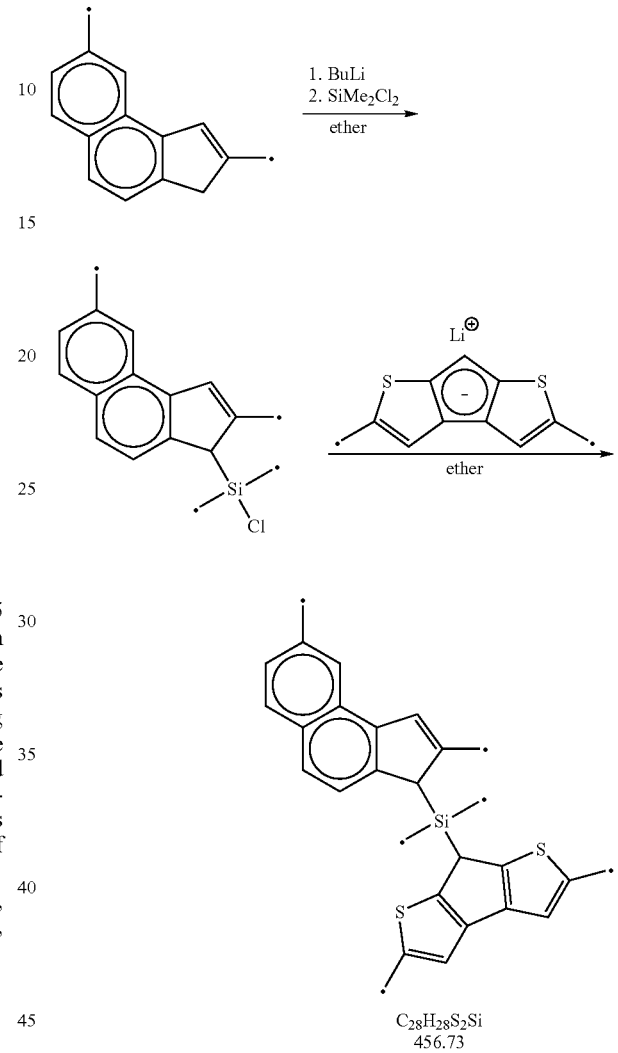

A solution of 2,8-dimethyl-3H-cyclopenta[a]naphthalene (0.43 g, 2.2 mmole) prepared as described above in ether (10 ml) was cooled to −40° C., and n-BuLi in hexane (1.6M, 1.4 ml, 2.2 mmole) was added. Resulting mixture was allowed to warm to room temperature, stirred for 1 h, cooled to −60° C., and SiMe$_2$Cl$_2$ (0.35 ml, 2.9 mmole) was added. Resulting mixture was allowed to warm to room temperature, stirred for 16 h, evaporated and dried. Dimethyldithiophenocyclopentadiene (0.45 g, 2.2 mmole) in ether (15 ml) was cooled to −40° C., and n-BuLi in hexane (1.6M, 1.4 ml, 2.2 mmole) was added. Resulting mixture was allowed to warm to room temperature, stirred for 1 h, and added to suspension of dimethylchlorosilyl derivative of 2,8-dimethyl-3H-cyclopenta[a]naphthalene in 10 ml of ether at −60° C. The resulting mixture was allowed to warm to room temperature, stirred for 16 h, evaporated and dried. The product was obtained by column chromatography (silica gel 60, hexane/CHCl$_3$ 8:1). The yield 0.82 g (82%) of yellow solid.

b) {μ-(η⁵-2,8-Dimethyl-3H-cyclopenta[a]naphth-3-yl)(η⁵-2,5-dimethyldithiophenocyclopentadien-7-yl)dimethylsilanediyl] dichlorozirconium (IV) (A2)

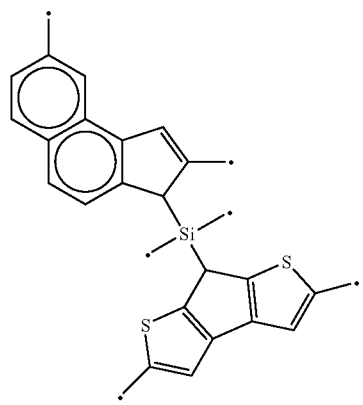

1. n-BuLi
2. ZrCl₄
ether
→

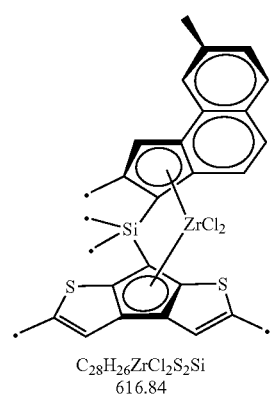

C₂₈H₂₆ZrCl₂S₂Si
616.84

(2,8-dimethyl-3H-cyclopenta[a]naphth-3-yl)(2,5-dimethyl dithiopheno cyclopentadien-7-yl)dimethylsilane (0.82 g, 1.8 mmole) obtained in step a) was dissolved in Et₂O (20 ml), cooled to −40° C., and n-BuLi (2.5 ml of 1.6M in hexane, 4 mmole) was added. Reaction mixture was allowed to warm to room temperature, stirred for 2 h, cooled to −60° C., and ZrCl₄ (0.44 g, 1.9 mmole) was added. Resulting mixture was allowed to warm to room temperature with stirring, stirred for additional 16 h. The resulting yellow precipitate was filtered off and recrystallized from CH₂Cl₂ giving yellow-orange product. The yield 0.82 g (74%).

¹H NMR (CD₂Cl₂, 20° C.) δ: 7.81 (s, 1H); 7.59 (d, 1H); 7.51 (d, 1H); 7.30 (d, 1H); 7.12 (d, 1H) {aromatic C₆ rings}; 6.79 (s, 2H); 6.57 (s, 1H) {C₅ rings}; 2.60 (s, 3H); 2.53 (s, 3H); 2.43 (s, 3H); 2.40 (s, 3H); {C—CH₃}; 1.32 (s, 3H); 1.18 (s, 3H) {Si—CH₃}.

Example 3

Synthesis of {μ-(η⁵-2-Methyl-8-phenyl-3H-cyclopenta[a]naphth-3-yl)(η⁵-2,5-dimethyldithiophenocyclopentadien-7-yl)dimethylsilanediyl] dichlorozirconium (IV) (A3)

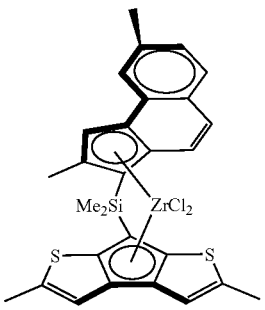

(A2)

a) 2,7-Dibromonaphthalene was obtained by known method starting from 2,7-naphthalenediol [Porzi G., Concilio C., J. Organomet. Chem., 128 (1977), 95-98]

b) 2-Bromo-7-methylnaphthalene

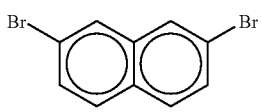

1. n-BuLi
2. CH₃I
ether
→

C₁₁H₉Br
221.09

Suspension of 2,7-dibromonaphthalene (61.4 g, 0.21 mole) in ether (400 ml) was cooled to −30° C., and n-BuLi (1.6M in hexane, 135 ml, 0.21 mole) was added. Reaction mixture was allowed to warm to room temperature, stirred for additional 2.5 h, cooled to −30° C., and CH₃I (13.5 ml, 0.21 mole) was added. Reaction mixture was allowed to warm to room temperature, stirred for additional 16 h, treated by water (100 ml). Organic layer was separated, water layer was extracted by ether (6×100 ml). Combined organic fraction was evaporated, giving practically pure solid product. The yield 38.1 g (82%).

¹H NMR (CDCl₃, 20° C.) δ: 7.93 (s, 1H); 7.70 (d, 1H); 7.52 (s, 1H); 7.50 (d, 1H); 7.35 (d, 1H) {aromatic C₆ rings}; 2.54 (s, 3H, —CH₃).

c) 2-Methyl-7-phenylnaphthalene

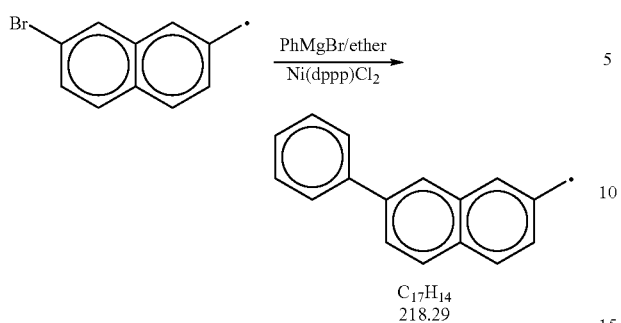

Solution of 2-bromo-7-methylnaphthalene (10 g, 45 mmole) in ether (100 ml) was cooled to −0° C., and Ni(dppp)Cl$_2$ and solution of PhLi (obtained from 1.3 g of Mg and 5.6 ml of PhBr in 55 ml of ether) were added subsequently. Reaction mixture was allowed to warm to room temperature, stirred for additional 4 h with heating, cooled room temperature, stirred for additional 16 h, and treated by water (100 ml). Organic layer was separated, water layer was extracted by ether (3×50 ml). Combined organic fraction was evaporated, giving practically pure solid product. The yield 9.23 g (94%).

$^1$H NMR (CDCl$_3$, 20° C.) δ: 8.10 (s, 1H); 7.92 (d, 1H); 7.83-7.71 (group of m, 5H); 7.53 (t, 2H); 7.43 (t, 1H); 7.37 (d, 1H) {aromatic C$_6$ rings}; 2.58 (s, 3H, —CH$_3$).

d) 2-(Bromomethyl)-7-phenylnaphthalene

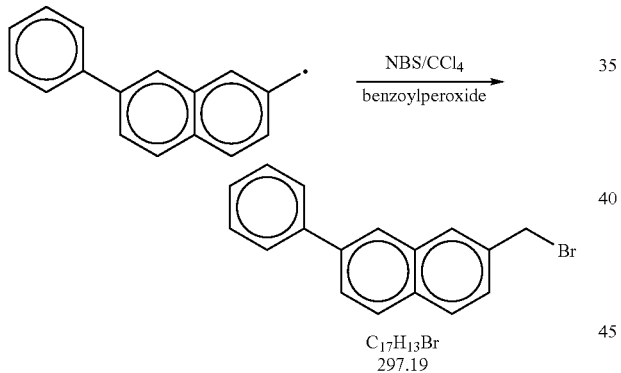

2-Methyl-7-phenylnaphthalene (5.4 g, 25 mmole) and N-bromosuccinimide (4.4 g, 25 mmole) were suspended in CCl$_4$ (60 ml). Benzoylperoxide (0.25 g) and Br$_2$ (20 mkl) were added, the mixture was refluxed for 3 h, filtered, evaporated and dried giving practically pure product. The yield 7.4 g (~100%).

$^1$H NMR (CDCl$_3$, 20° C.) δ: 8.40 (s, 1H); 7.94-7.73 (group of m, 6H); 7.53 (m, 3H); 7.44 (t, 1H{aromatic C$_6$ rings}; 4.71 (s, 2H, —CH$_2$).

e) 2-Methyl-3-(7-phenyl-2-naphthyl)propanoic acid

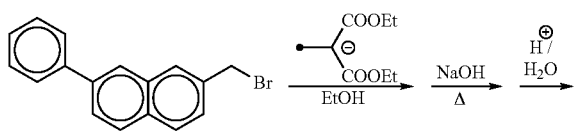

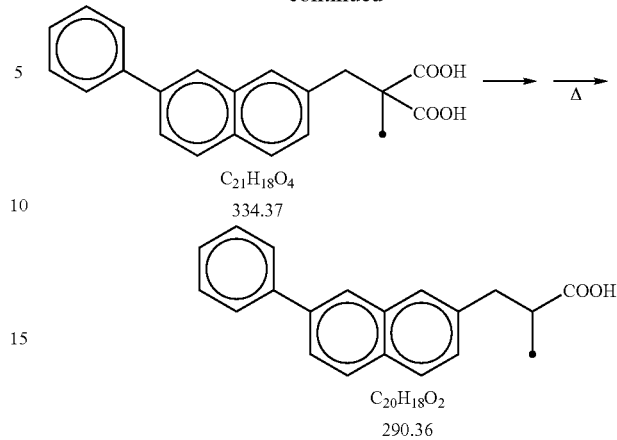

Diethylmethylmalonate (4.35 g, 25 mmole) was added to the solution of EtONa (1.7 g, 25 mmole) in ethanol (80 ml). The resulting mixture was stirred for 2 h, and 2-(Bromomethyl)-7-phenylnaphthalene (7.4 g, 25 mmole) was added. The resulting mixture was refluxed for 6 h, cooled, treated by NaOH (4 g in 10 ml of H$_2$O) and refluxed for 6 h.

After cooling, aq. HCl was added to pH ~1. Resulting precipitate was filtered off, leading pure 2-methyl-2-[(7-phenyl-2-naphthyl)methyl]malonic acid. The yield 7.2 g (86%).

$^1$H NMR (DMSO-d$_6$, 20° C.) δ: 12.9 (broad, 2H, —COOH); 8.12 (s, 1H); 7.97 (d, 1H); 7.86 (d, 1H); 7.80 (m, 4H); 7.52 (t, 2H); 7.41 (t, 1H); 7.35 (d, 1H) {aromatic C$_6$ rings}; 3.28 (s, 2H, —CH$_2$); 1.25 (s, 3H, —CH$_3$).

2-Methyl-3-(7-phenyl-2-naphthyl)propanoic acid (6.25 g) was obtained by heating of dicarboxylic acid (150-160° C., 30 min).

$^1$H NMR (CDCl$_3$, 20° C.) δ: 11.5-10 (broad, 1H, —COOH); 8.15 (s, 1H); 7.92 (d, 1H); 7.83 (d, 1H); 7.76 (m, 4H); 7.52 (t, 2H); 7.42 (t, 1H); 7.36 (d, 1H) {aromatic C$_6$ rings}; 3.30 (m, 1H); 2.90 (m, 2H) {—CHCH$_2$—}; 1.25 (d, 3H, —CH$_3$).

f) 2-Methyl-8-phenyl-2,3-dihydro-1H-cyclopenta[a]naphthalen-1-one

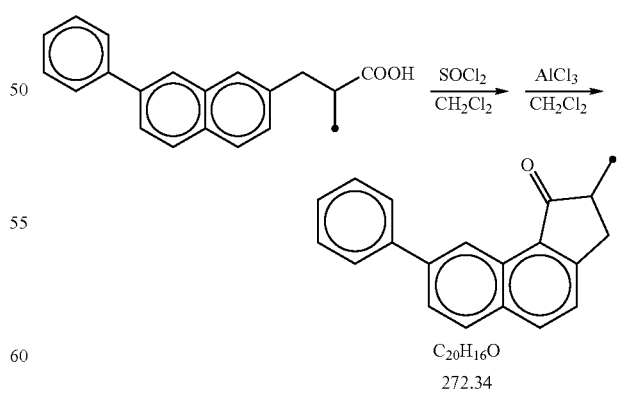

2-Methyl-3-(7-phenyl-2-naphthyl)propanoic acid (6.25 g, 21.5 mmole) was suspended in CH$_2$Cl$_2$ (20 ml), and SOCl$_2$ (2.9 ml, 40 mmole) and 0.05 ml of DMF were added. The resulting mixture was stirred for 2 h at room temperature, refluxed for additional 1 h, evaporated and dried in vacuo. AlCl$_3$ (4.3 g, 33 mmol) was suspended in CH$_2$Cl$_2$ (40 ml), and solution of obtained chloroanhydride in CH$_2$Cl$_2$ (20 ml) was added at 0° C. within 0.5 h. The resulting mixture was allowed to warm to room temperature, stirred for additional 2 h, and poured into ice/HCl (~200 g+40 ml). The resulting mixture was extracted by CH$_2$Cl$_2$ (4×50 ml). Combined organic phase was washed by aq. KHCO$_3$, dried over MgSO$_4$, evaporated and dried in vacuo giving practically pure solid product. The yield 5.45 g (92%).

$^1$H NMR (CDCl$_3$, 20° C.) δ: 9.48 (s, 1H); 8.07 (d, 1H); 7.70 (d, 1H); 7.85 (m, 3H); 7.53 (m, 3H); 7.43 (t, 1H) {aromatic C$_6$ rings}; 3.50 (m, 1H); 2.85 (m, 2H) {—CHCH$_2$—}; 1.41 (d, 3H, —CH$_3$).

g) 2-Methyl-8-phenyl-3H-cyclopenta[a]naphthalene

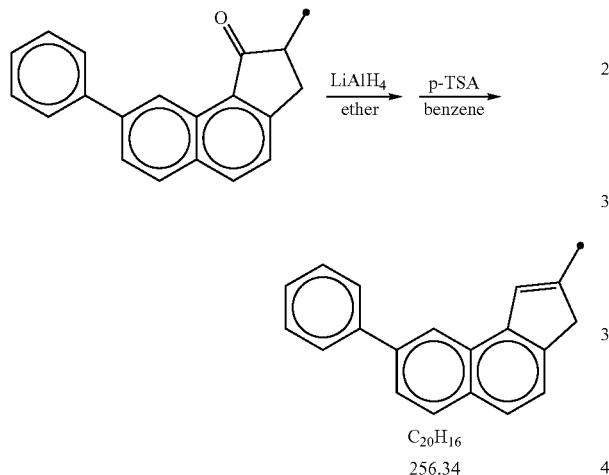

2-Methyl-8-phenyl-2,3-dihydro-1H-cyclopenta[a]naphthalen-1-one (5.45 g, 20 mmole) in Et$_2$O (50 ml) was added dropwise to cooled (–40° C.) suspension of LiAlH$_4$ (0.23 g, 6 mmole) in Et$_2$O (50 ml). The resulting mixture was allowed to warm to room temperature and stirred for additional 2 h. Then H$_2$O (10 ml) and 10M HCl (5 ml) were added, the resulting mixture was poured into CH$_2$Cl$_2$ (300 ml). The organic phase was washed by water (50 ml), 5% aq. KHCO$_3$ (50 ml), dried over MgSO$_4$ and evaporated giving white crystalline alcohol. The 250 ml round-bottomed flack was sparged with argon; benzene (100 ml) and p-TSA (0.2 g) were added, and resulting solution was refluxed with Dine-Stark head with stirring (control by TLC, benzene/EtOAc 4:1) within 1.5 h. Then the resulting yellow solution was washed by water, aq. KHCO$_3$, water, dried over MgSO$_4$, passed through small amount of silica gel and evaporated giving 4.8 g (94%) of the product.

$^1$H NMR (CDCl$_3$, 20° C.) δ: 8.30 (s, 1H); 7.98 (d, 1H); 7.82 (dd, 2H); 7.75 (d, 1H); 7.68 (d, 1H); 7.60 (d, 1H); 7.55 (t, 2H); 7.44 (d, 1H); 7.20 (s, 1H) {—CH=}; 3.51 (s, 2H, —CH$_2$—); 2.33 (s, 3H, —CH$_3$).

h) (2-Methyl-8-phenyl-3H-cyclopenta[a]naphth-3-yl) (2,5-dimethyldithiophenocyclopentadien-7-yl)dimethylsilane

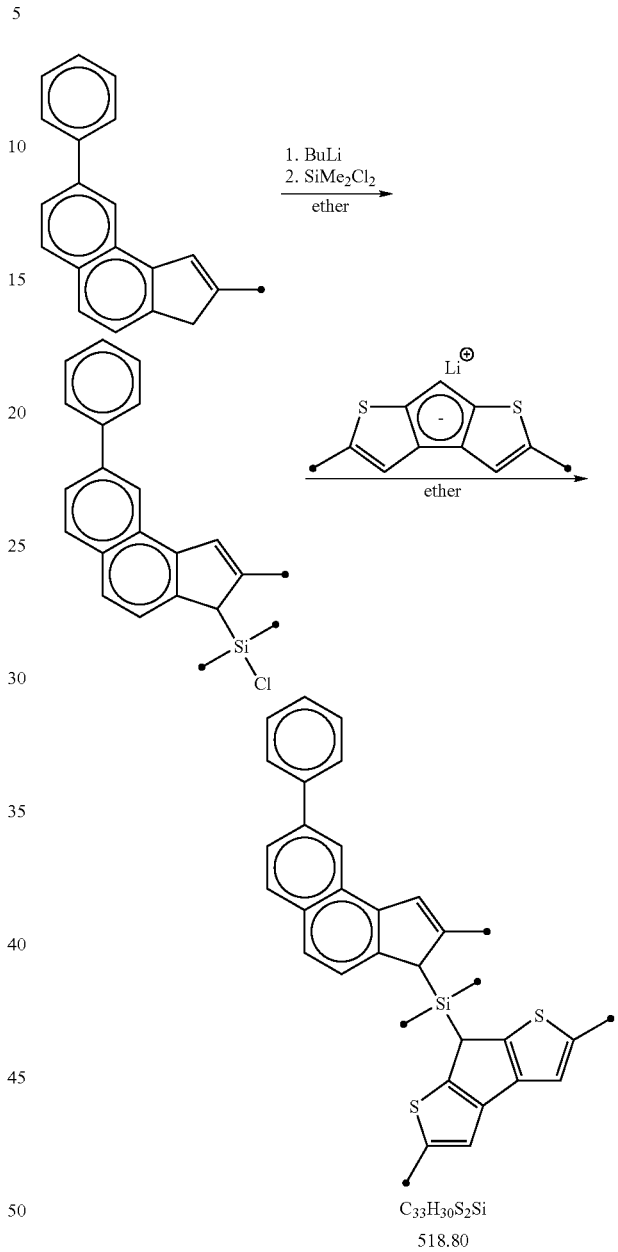

Solution of 2-methyl-8-phenyl-3H-cyclopenta[a]naphthalene (2.56 g, 10 mmole) in ether (50 ml) was cooled to –40° C., and n-BuLi in hexane (1.6M, 6.3 ml, 10 mmole) was added.

Resulting mixture was allowed to warm to room temperature, stirred for 1 h, cooled to –60° C., and SiMe$_2$Cl$_2$ (1.33 ml, 11 mmole) was added. Resulting mixture was allowed to warm to room temperature, stirred for 16 h, evaporated and dried. Dimethyldithiophenocyclopentadiene (2.06 g, 10 mmole) in ether (40 ml) was cooled to –40° C., and n-BuLi in hexane (1.6M, 6.3 ml, 10 mmole) was added. Resulting mixture was allowed to warm to room temperature, stirred for 1 h, and added to suspension of dimethylchlorosilyl derivative of 2-methyl-8-phenyl-3H-cyclopenta[a]naphthalene in 50 ml of ether at –60° C. The resulting mixture was allowed to warm to room temperature, stirred for 16 h, evaporated and dried. The product was obtained by crystallization from hexane as a single isomer. The yield 2.28 g (44%).

$^1$H NMR (CDCl$_3$, 20° C.) δ: 8.39 (s, 1H); 7.99 (d, 1H); 7.81 (dd, 2H); 7.78 (d, 1H); 7.63 (m, 2H); 7.56 (t, 2H); 7.44 (t, 1H); 7.36 (s, 1H); 6.94 (s, 1H); 6.90 (s, 1H) {—CH=}; 4.19 (s, 1H); 4.10 (s, 1H) {>CH—}; 2.63 (s, 3H); 2.58 (s, 3H); 2.42 (s, 3H) {C—CH$_3$}; −0.31 (s, 3H); −0.33 (s, 3H) {Si—CH$_3$}.

i) {μ-(η$^5$-2-Methyl-8-phenyl-3H-cyclopenta[a]naphth-3-yl)(η$^5$-2,5-dimethyldithiophenocyclopentadien-7-yl)dimethylsilanediyl]dichiorozirconium (IV)

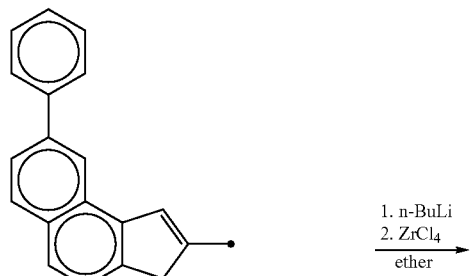

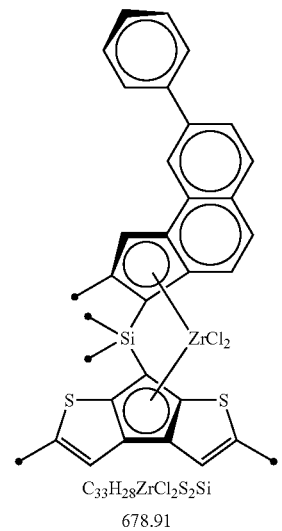

C$_{33}$H$_{28}$ZrCl$_2$S$_2$Si
678.91

(2-Methyl-8-phenyl-3H-cyclopenta[a]naphth-3-yl)(2,5-dimethyl-dithipheno-cyclopentadien-7-yl)dimethylsilane (2.28 g, 4.39 mmole) was suspended in Et$_2$O (60 ml), cooled to −40° C., and n-BuLi (5.6 ml of 1.6M in hexane, 9 mmole) was added. Reaction mixture was allowed to warm to room temperature, stirred for 2 h, cooled to −60° C., and ZrCl$_4$ (1.05 g, 4.5 mmole) was added. Resulting mixture was allowed to warm to room temperature with stirring, stirred for additional 16 h. The resulting yellow precipitate was filtered off and purified by 20-times extraction by CH$_2$Cl$_2$ with subsequent concentration of the solution giving yellow-orange product. The yield 1.97 g (66%).

Polymerization Examples

General Procedure

The catalyst mixture was prepared by dissolving the amount of the metallocene indicated in table 1 in 5 ml of toluene with the proper amount of the methylalumoxane (MAO) solution (30% by weight in toluene)(Al/Zr molar ratio=500) obtaining a solution which was stirred for 10 min at room temperature before being injected into the autoclave.

2 mmol of Al(i-Bu)$_3$ (as a 1M solution in hexane) and 700 g of propylene were charged at room temperature in a 2.4-L jacketed stainless-steel autoclave, equipped with magnetically driven stirrer and a 35-mL stainless-steel vial, connected to a thermostat for temperature control, previously purified by washing with an Al(i-Bu)$_3$ solution in hexanes and dried at 50° C. in a stream of propylene. The autoclave was then thermostatted at 70° C., and then the toluene solution containing the catalyst/cocatalyst mixture was injected in the autoclave by means of nitrogen pressure through the stainless-steel vial, and the polymerization carried out at constant temperature for 1 hour. The polymerization was stopped by pressurizing CO into the reactor. After venting the unreacted monomer and cooling the reactor to room temperature, the polymer was dried under reduced pressure at 60° C. The polymerization results are reported in table 1.

TABLE 1

| Ex | metall. (mg) | Activity Kg/g$_{cat}$·h | η dL/g | Tm(II) (° C.) |
|---|---|---|---|---|
| 1 | A1 (1)$^{a)}$ | 319 | 2.1 | 144.7 |
| 2* | C1 (0.5) | 220 | 1.8 | 144 |
| 3* | C2 (0.5)$^{b)}$ | 200 | 2.1 | 143.5 |

*comparative
$^{a)}$mixture of rac meso isomers (rac:meso 6:4);
$^{b)}$mixture of rac meso isomers (rac:meso 5:1);

From table 1 clearly results that the compound A1 even if it is used in rac, meso mixture (the meso form has an activity lower or it is inactive with respect to the rac form) shows a polymerization activity higher than the compound C1 and C2.

The invention claimed is:
1. A metallocene compound of formula (IV):

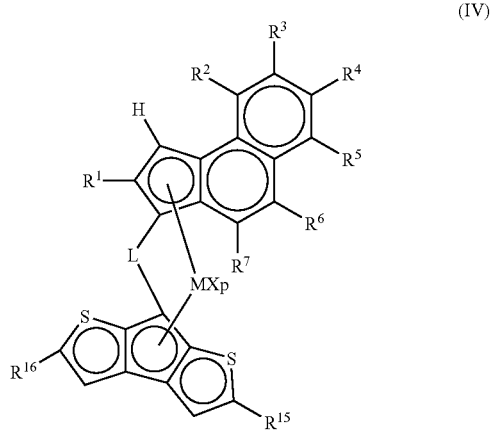

(IV)

wherein:
M is a transition metal selected from group 3, 4, 5, 6 or a lanthanide or an actinide group in the Periodic Table of Elements;

p is an integer from 0 to 3, wherein p is equal to a formal oxidation state of M minus 2;

X, is the same or different, and is hydrogen, a halogen, R, OR, $OSO_2CF_3$, OCOR, SR, $NR_2$ or $PR_2$, wherein R is a $C_1$-$C_{40}$ hydrocarbon group optionally comprising at least one heteroatom belonging to groups 13-17 of the Periodic Table of Elements; or two X can optionally form a substituted or unsubstituted butadienyl radical, or a OR'O group, wherein R' is a divalent radical selected from a $C_1$-$C_{40}$ alkylidene radical, a $C_6$-$C_{40}$ arylidene radical, a $C_7$-$C_{40}$ alkylarylidene radical or a $C_7$-$C_{40}$ arylalkylidene radical;

L is a divalent bridging group selected from a $C_1$-$C_{20}$ alkylidene radical, a $C_3$-$C_{20}$ cycloalkylidene radical, a $C_6$-$C_{20}$ arylidene radical, a $C_7$-$C_{20}$ alkylarylidene radical, or a $C_7$-$C_{20}$ arylalkylidene radical optionally comprising at least one heteroatom belonging to groups 13-17 of the Periodic Table of Elements, or a silylidene radical comprising up to 5 silicon atoms;

$R^1$ is a $C_1$-$C_{40}$ hydrocarbon group optionally comprising at least one heteroatom belonging to groups 13-17 of the Periodic Table of Elements;

$R^3$ is a $C_1$-$C_{40}$ hydrocarbon group optionally comprising at least one heteroatom belonging to groups 13-17 of the Periodic Table of Elements;

$R^2$, $R^4$ and $R^5$, are the same or different from each other, and are hydrogen or $C_1$-$C_{40}$ hydrocarbon groups optionally comprising at least one heteroatom belonging to groups 13-17 of the Periodic Table of Elements, with the proviso that at least one among $R^2$, $R^4$ and $R^5$ is hydrogen;

$R^6$ and $R^7$, are the same or different from each other, and are hydrogen or $C_1$-$C_{40}$ hydrocarbon groups optionally comprising at least one heteroatom belonging to groups 13-17 of the Periodic Table of Elements;

$R^{15}$ and $R^{16}$, are the same or different from each other, and are hydrogen or $C_1$-$C_{40}$ hydrocarbon groups optionally comprising at least one heteroatom belonging to groups 13-17 of the Periodic Table of Elements; and $R^3$ with $R^4$ and/or $R^4$ with $R^5$ can optionally join to form a aliphatic or aromatic 3-7 membered ring optionally comprising at least one heteroatom belonging to groups 13-16 of the Periodic Table of Elements, the aliphatic or aromatic 3-7 membered ring optionally can comprise one or more hydrocarbon substituents comprising from 1 to 20 carbon atoms.

2. The metallocene compound of claim 1, wherein:
M is titanium, zirconium or hafnium;
p is 2;
X is hydrogen, a halogen, or R;
R is a linear or branched, cyclic or acyclic $C_1$-$C_{40}$-alkyl radical, $C_2$-$C_{40}$ alkenyl radical, $C_2$-$C_{40}$ alkynyl radical, $C_6$-$C_{40}$-aryl radical, $C_7$-$C_{40}$-alkylaryl radical or $C_7$-$C_{40}$-arylalkyl radical, optionally comprising at least one heteroatom belonging to groups 13-17 of the Periodic Table of Elements;
L is $Z(R'')_2$, wherein Z is a carbon or a silicon atom, and R'' is a linear or branched, cyclic or acyclic $C_1$-$C_{10}$-alkyl radical, $C_2$-$C_{10}$ alkenyl radical, $C_2$-$C_{10}$ alkynyl radical, $C_6$-$C_{10}$-aryl radical, $C_7$-$C_{10}$-alkylaryl radical, or $C_7$-$C_{10}$-arylalkyl radical optionally comprising at least one heteroatom belonging to groups 13-17 of the Periodic Table of Elements.

3. The metallocene compound of claim 1, wherein:
$R^1$ is a linear or branched $C_1$-$C_{20}$-alkyl radical;
$R^3$ is a linear or branched $C_1$-$C_{20}$-alkyl radical or a $C_6$-$C_{40}$-aryl, radical;
$R^2$, $R^4$ and $R^5$ are hydrogen; and $R^6$ and $R^7$ are hydrogen or a linear or branched $C_1$-$C_{20}$-alkyl radical.

4. The metallocene compound according to claim 1, wherein $R^{15}$ and $R^{16}$ are linear or branched $C_1$-$C_{40}$-alkyl radicals optionally comprising at least one heteroatom belonging to groups 13-17 of the Periodic Table of Elements.

5. A process for preparing a metallocene compound of formula (IV):

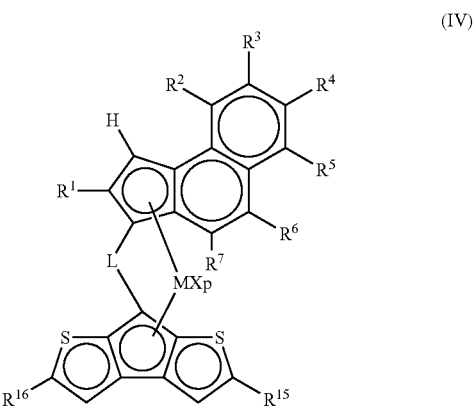

wherein:
M is a transition metal selected from group 3, 4, 5, 6 or a lanthanide or an actinide group in the Periodic Table of Elements;

p is an integer from 0 to 3, wherein p is equal to a formal oxidation state of M minus 2;

X, is the same or different, and is hydrogen, a halogen, R, OR, $OSO_2CF_3$, OCOR, SR, $NR_2$ or $PR_2$, wherein R is a $C_1$-$C_{40}$ hydrocarbon group optionally comprising at least one heteroatom belonging to groups 13-17 of the Periodic Table of Elements; or two X can optionally form a substituted or unsubstituted butadienyl radical, or a OR'O group, wherein R' is a divalent radical selected from a $C_1$-$C_{40}$ alkylidene radical, a $C_6$-$C_{40}$ arylidene radical, a $C_7$-$C_{40}$ alkylarylidene radical or a $C_7$-$C_{40}$ arylalkylidene radical;

L is a divalent bridging group selected from a $C_1$-$C_{20}$ alkylidene radical, a $C_3$-$C_{20}$ cycloalkylidene radical, a $C_6$-$C_{20}$ arylidene radical, a $C_7$-$C_{20}$ alkylarylidene radical, or a $C_7$-$C_{20}$ arylalkylidene radical optionally comprising at least one heteroatom belonging to groups 13-17 of the Periodic Table of Elements, or a silylidene radical comprising up to 5 silicon atoms;

$R^1$ is a $C_1$-$C_{40}$ hydrocarbon group optionally comprising at least one heteroatom belonging to groups 13-17 of the Periodic Table of Elements;

$R^3$ is a $C_1$-$C_{40}$ hydrocarbon group optionally comprising at least one heteroatom belonging to groups 13-17 of the Periodic Table of Elements;

$R^2$, $R^4$ and $R^5$, are the same or different from each other, and are hydrogen or $C_1$-$C_{40}$ hydrocarbon groups optionally comprising at least one heteroatom belonging to groups 13-17 of the Periodic Table of Elements, with the proviso that at least one among $R^2$, $R^4$ and $R^5$ is hydrogen;

$R^6$ is hydrogen or $C_1$-$C_{40}$ hydrocarbon groups optionally comprising at least one heteroatom belonging to groups 13-17 of the Periodic Table of Elements;

$R^7$ is hydrogen;

$R^{15}$ and $R^{16}$, are the same or different from each other, and are hydrogen or $C_1$-$C_{40}$ hydrocarbon groups optionally comprising at least one heteroatom belonging to groups 13-17 of the Periodic Table of Elements; and $R^3$ with $R^4$ and/or $R^4$ with $R^5$ can optionally join to form a aliphatic or aromatic 3-7 membered ring optionally comprising at least one heteroatom belonging to groups 13-16 of the Periodic Table of Elements, the aliphatic or aromatic 3-7 membered ring optionally can comprise one or more hydrocarbon substituents comprising from 1 to 20 carbon atoms;

the process comprising:

contacting a compound of formula (IVa)

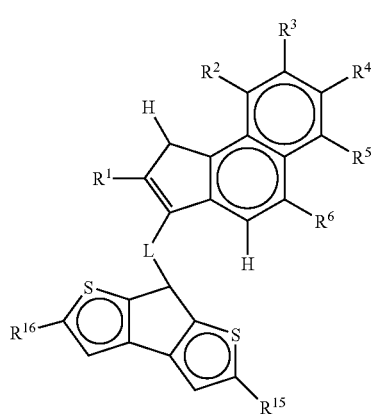

(IVa)

and/or its double bond isomers with a base selected from $T_jB$, $TMgT^1$, sodium hydride, potassium hydride, metallic sodium, metallic potassium, or combinations thereof to form a metallocene compound product, wherein:

L is a divalent bridging group selected from a $C_1$-$C_{20}$ alkylidene radical, a $C_3$-$C_{20}$ cycloalkylidene radical, a $C_6$-$C_{20}$ arylidene radical, a $C_7$-$C_{20}$ alkylarylidene radical, or a $C_7$-$C_{20}$ arylalkylidene radical optionally comprising at least one heteroatom belonging to groups 13-17 of the Periodic Table of Elements, or a silylidene radical comprising up to 5 silicon atoms;

$R^1$ is a $C_1$-$C_{40}$ hydrocarbon group optionally comprising at least one heteroatom belonging to groups 13-17 of the Periodic Table of Elements;

$R^3$ is a $C_1$-$C_{40}$ hydrocarbon group optionally comprising at least one heteroatom belonging to groups 13-17 of the Periodic Table of Elements;

$R^2$, $R^4$ and $R^5$, are the same or different from each other, and are hydrogen or $C_1$-$C_{40}$ hydrocarbon groups optionally comprising at least one heteroatom belonging to groups 13-17 of the Periodic Table of Elements, with the proviso that at least one among $R^2$, $R^4$ and $R^5$ is hydrogen;

$R^6$ and $R^7$, are the same or different from each other, and are hydrogen or $C_1$-$C_{40}$ hydrocarbon groups optionally comprising at least one heteroatom belonging to groups 13-17 of the Periodic Table of Elements;

$R^{15}$ and $R^{16}$, are the same or different from each other, and are hydrogen or $C_1$-$C_{40}$ hydrocarbon groups optionally comprising at least one heteroatom belonging to groups 13-17 of the Periodic Table of Elements; and $R^3$ with $R^4$ and/or $R^4$ with $R^5$ can optionally join to form a aliphatic or aromatic 3-7 membered ring optionally comprising at least one heteroatom belonging to groups 13-16 of the Periodic Table of Elements, the aliphatic or aromatic 3-7 membered ring optionally can comprise one or more hydrocarbon substituents comprising from 1 to 20 carbon atoms B is an alkali or alkaline earth metal;

j is 1 or 2, wherein j is equal to 1 when B is an alkaline metal, and j is equal to 2 when B is an alkali-earth metal;

T is a linear or branched, cyclic or acyclic $C_1$-$C_{20}$-alkyl radical, $C_6$-$C_{20}$-aryl radical, $C_7$-$C_{20}$-alkylaryl radical, or $C_7$-$C_{20}$-arylalkyl radical, optionally comprising one or more Si or Ge atoms;

$T^1$ is a halogen or OR''', wherein R''' is a linear or branched, cyclic or acyclic $C_1$-$C_{40}$-alkyl radical, $C_6$-$C_{40}$-aryl radical, $C_7$-$C_{40}$-alkylaryl radical or $C_7$-$C_{40}$-arylalkyl radical, optionally comprising at least one heteroatom belonging to groups 13-17 of the Periodic Table of Elements, wherein a molar ratio between the base and a ligand of the formula (IVa) is at least 2:1; and contacting the metallocene compound product with a compound of formula $MX_{p+2}$, wherein:

M is a transition metal selected from group 3, 4, 5, 6 or a lanthanide or an actinide group in the Periodic Table of Elements;

p is an integer from 0 to 3, wherein p is equal to a formal oxidation state of M minus 2; and X, is the same or different, and is hydrogen, a halogen, R, OR, $OSO_2CF_3$, OCOR, SR, $NR_2$ or $PR_2$, wherein R is a $C_1$-$C_{40}$ hydrocarbon group optionally comprising at least one heteroatom belonging to groups 13-17 of the Periodic Table of Elements; or two X can optionally form a substituted or unsubstituted butadienyl radical, or a OR'O group, wherein R' is a divalent radical selected from a $C_1$-$C_{40}$ alkylidene radical, a $C_6$-$C_{40}$ arylidene radical, a $C_7$-$C_{40}$ alkylarylidene radical or a $C_7$-$C_{40}$ arylalkylidene radical.

6. The process for preparing the metallocene compound of claim 5, wherein B is lithium.

7. The process for preparing the metallocene compound of claim 5, wherein T is a methyl radical or butyl radical.

8. A ligand of formula (IVa) and its double bonds isomers

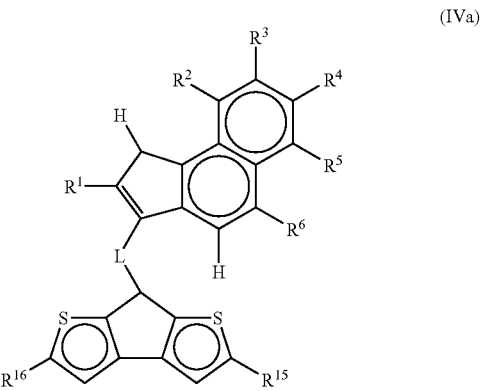

(IVa)

wherein:

L is a divalent bridging group selected from a $C_1$-$C_{20}$ alkylidene radical, a $C_3$-$C_{20}$ cycloalkylidene radical, a $C_6$-$C_{20}$ arylidene radical, a $C_7$-$C_{20}$ alkylarylidene radical, or a $C_7$-$C_{20}$ arylalkylidene radical optionally comprising at least one heteroatom belonging to groups 13-17 of the Periodic Table of Elements, or a silylidene radical comprising up to 5 silicon atoms;

$R^1$ is a $C_1$-$C_{40}$ hydrocarbon group optionally comprising at least one heteroatom belonging to groups 13-17 of the Periodic Table of Elements;

$R^3$ is a $C_1$-$C_{40}$ hydrocarbon group optionally comprising at least one heteroatom belonging to groups 13-17 of the Periodic Table of Elements;

$R^2$, $R^4$ and $R^5$, are the same or different from each other, and are hydrogen or $C_1$-$C_{40}$ hydrocarbon groups optionally comprising at least one heteroatom belonging to groups 13-17 of the Periodic Table of Elements, with the proviso that at least one among $R^2$, $R^4$ and $R^5$ is hydrogen;

$R^6$ is hydrogen or $C_1$-$C_{40}$ hydrocarbon groups optionally comprising at least one heteroatom belonging to groups 13-17 of the Periodic Table of Elements;

$R^3$ with $R^4$ and/or $R^4$ with $R^5$ can optionally join to form a aliphatic or aromatic 3-7 membered ring optionally comprising at least one heteroatom belonging to groups 13-16 of the Periodic Table of Elements, the aliphatic or aromatic 3-7 membered ring optionally can comprise one or more hydrocarbon substituents comprising from 1 to 20 carbon atoms; and $R^{15}$ and $R^{16}$, are the same or different from each other, and are hydrogen or $C_1$-$C_{40}$ hydrocarbon groups optionally comprising at least one heteroatom belonging to groups 13-17 of the Periodic Table of Elements.

9. The ligand of claim 8, wherein:

L is $Z(R'')_2$, wherein Z is a carbon or a silicon atom, and R" is a linear or branched, cyclic or acyclic $C_1$-$C_{10}$-alkyl radical, $C_2$-$C_{10}$ alkenyl radical, $C_2$-$C_{10}$ alkynyl radical, $C_6$-$C_{10}$-aryl radical, $C_7$-$C_{10}$-alkylaryl radical, or $C_7$-$C_{10}$-arylalkyl radical optionally comprising at least one heteroatom belonging to groups 13-17 of the Periodic Table of Elements.

10. The ligand of claim 8, wherein:

$R^1$ is a linear or branched $C_1$-$C_{20}$-alkyl radical;

$R^3$ is a linear or branched $C_1$-$C_{20}$-alkyl radical or a $C_6$-$C_{40}$-aryl, radical;

$R^2$, $R^4$ and $R^5$ are hydrogen; and $R^6$ is hydrogen or a linear or branched $C_1$-$C_{20}$-alkyl radical.

11. A catalyst system obtained by contacting:

a) at least one metallocene compound of formula (IV)

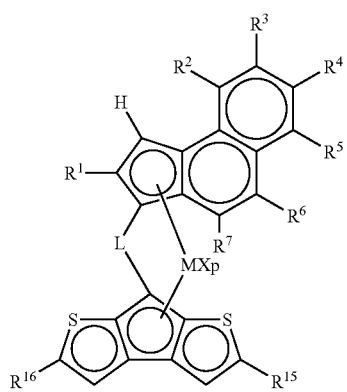

(IV)

wherein:

M is a transition metal selected from group 3, 4, 5, 6 or a lanthanide or an actinide group in the Periodic Table of Elements;

p is an integer from 0 to 3, wherein p is equal to a formal oxidation state of M minus 2;

X, is the same or different, and is hydrogen, a halogen, R, OR, $OSO_2CF_3$, OCOR, SR, $NR_2$ or $PR_2$, wherein R is a $C_1$-$C_{40}$, hydrocarbon group optionally comprising at least one heteroatom belonging to groups 13-17 of the Periodic Table of Elements; or two X can optionally form a substituted or unsubstituted butadienyl radical, or a OR'O group, wherein R' is a divalent radical selected from a $C_1$-$C_{40}$ alkylidene radical, a $C_6$-$C_{40}$ arylidene radical, a $C_7$-$C_{40}$ alkylarylidene radical or a $C_7$-$C_{40}$ arylalkylidene radical;

L is a divalent bridging group selected from a $C_1$-$C_{20}$ alkylidene radical, a $C_3$-$C_{20}$ cycloalkylidene radical, a $C_6$-$C_{20}$ arylidene radical, a $C_7$-$C_{20}$ alkylarylidene radical, or a $C_7$-$C_{20}$ arylalkylidene radical optionally comprising at least one heteroatom belonging to groups 13-17 of the Periodic Table of Elements, or a silylidene radical comprising up to 5 silicon atoms;

$R^1$ is a $C_1$-$C_{40}$ hydrocarbon group optionally comprising at least one heteroatom belonging to groups 13-17 of the Periodic Table of Elements;

$R^3$ is a $C_1$-$C_{40}$ hydrocarbon group optionally comprising at least one heteroatom belonging to groups 13-17 of the Periodic Table of Elements;

$R^2$, $R^4$ and $R^5$, are the same or different from each other, and are hydrogen or $C_1$-$C_{40}$ hydrocarbon groups optionally comprising at least one heteroatom belonging to groups 13-17 of the Periodic Table of Elements, with the proviso that at least one among $R^2$, $R^4$ and $R^5$ is hydrogen;

$R^6$ and $R^7$, are the same or different from each other, and are hydrogen or $C_1$-$C_{40}$ hydrocarbon groups optionally comprising at least one heteroatom belonging to groups 13-17 of the Periodic Table of Elements;

$R^{15}$ and $R^{16}$, are the same or different from each other, and are hydrogen or $C_1$-$C_{40}$ hydrocarbon groups optionally comprising at least one heteroatom belonging to groups 13-17 of the Periodic Table of Elements; and $R^3$ with $R^4$ and/or $R^4$ with $R^5$ can optionally join to form a aliphatic or aromatic 3-7 membered ring optionally comprising at least one heteroatom belonging to groups 13-16 of the Periodic Table of Elements, the aliphatic or aromatic 3-7 membered ring optionally can comprise one or more hydrocarbon substituents comprising from 1 to 20 carbon atoms;

b) at least one alumoxane, or a compound able to form an alkylmetallocene cation; and c) optionally an organo aluminium compound.

12. A process for (co)polymerizing olefins comprising from 2 to 20 carbon atoms comprising contacting one or more of the olefins under polymerization conditions with the catalyst system of claim 11.

13. The process according to claim 12, wherein the olefins are alpha-olefins comprising from 2 to 20 carbon atoms.

14. The process according to claim 12, wherein the olefins are selected from propylene, ethylene, 1-butene, or combinations thereof.

* * * * *